(12) United States Patent
Shibata et al.

(10) Patent No.: US 8,062,310 B2
(45) Date of Patent: Nov. 22, 2011

(54) CLIPPING INSTRUMENT FOR AN ENDOSCOPIC SURGICAL DEVICE

(75) Inventors: Hiroaki Shibata, Saitama (JP); Tomohiro Kawano, Tokyo (JP)

(73) Assignee: Hoya Corporation, Tokyo (JP)

( * ) Notice: Subject to any disclaimer, the term of this patent is extended or adjusted under 35 U.S.C. 154(b) by 663 days.

(21) Appl. No.: 11/934,997

(22) Filed: Nov. 5, 2007

(65) Prior Publication Data
US 2008/0114377 A1     May 15, 2008

(30) Foreign Application Priority Data
Nov. 9, 2006   (JP) ................... 2006-303459

(51) Int. Cl.
*A61B 17/10*     (2006.01)
(52) U.S. Cl. ..................... 606/142; 227/175.1
(58) Field of Classification Search .......... 606/139, 606/142–143, 151, 157, 219, 158; 227/175.1; 623/23.72; 24/560, 703.1
See application file for complete search history.

(56) References Cited

U.S. PATENT DOCUMENTS

| | | | |
|---|---|---|---|
| 6,991,634 B2 * | 1/2006 | Sugiyama et al. | ............ 606/142 |
| 2002/0045909 A1 * | 4/2002 | Kimura et al. | ................ 606/151 |
| 2002/0133178 A1 * | 9/2002 | Muramatsu et al. | .......... 606/142 |
| 2005/0261735 A1 | 11/2005 | Shibata | |
| 2006/0271072 A1 | 11/2006 | Hummel et al. | |

FOREIGN PATENT DOCUMENTS

| | | |
|---|---|---|
| JP | 2003-144444 | 5/2003 |
| JP | 2004-73646 | 3/2004 |
| JP | 2004-351211 | 12/2004 |
| JP | 2005-013540 | 1/2005 |
| JP | 2006-87537 | 4/2006 |
| JP | 2006-087537 | 4/2006 |
| WO | 2005/046489 | 5/2005 |

OTHER PUBLICATIONS

English language Abstract of JP 2006-087537.
English language Abstract of JP 2005-013540.

* cited by examiner

*Primary Examiner* — Victor Nguyen
(74) *Attorney, Agent, or Firm* — Greenblum & Bernstein P.L.C.

(57) ABSTRACT

A clipping instrument for an endoscope is provided. The clipping instrument includes a flexible sheath and at least one clip assembly with a pair of openable and closable clipping arms. The clip assembly is arranged in vicinity to a distal end portion of the flexible sheath with the clipping arms closed. The clipping arms are configured to be protruded forward to open outside the flexible sheath and to be closed to clip onto a treatment object outside the flexible sheath. The clipping instrument further includes an operating wire, which is configured to be forwarded and retracted to operate the pair of arms to be opened and closed. The clip assembly includes a bendable portion, which corresponds to a position of a shaft to support the clipping arms. The clip assembly can be arbitrarily bended at the bendable portion.

2 Claims, 9 Drawing Sheets

CLIPPING INSTRUMENT FOR AN
ENDOSCOPIC SURGICAL DEVICE

BACKGROUND OF THE INVENTION

The present invention relates to a surgical device having a clipping instrument to be inserted through a forceps channel of an endoscope for in vivo hemostasis and marking operations.

Generally, in an endoscopic surgical device, a clipping instrument is arranged at a distal end of a flexible sheath, which is inserted through a forceps channel of an endoscope, with a clip thereof being closed. The clipping instrument is designed such that as an operating wire being detachably connected to the clip, axially movable in the flexible sheath, is forwarded, the clip is protruded accordingly from the distal end of the flexible sheath and opens like a pair of pincers.

Further, the clip is forcibly closed by an operation through the operating wire to clutch onto body tissue and detached therein from the operating wire to be left clutched during the surgery. Thus, an endoscopic clipping operation is conducted.

However, retracting the clipping instrument out of the forceps channel and reattaching a new clip to the operating wire each time the clip is detached can be troublesome. Therefore, a clipping instrument having a plurality of clips aligned in line inside the flexible sheath is provided so that the clipping operations can be successively conducted without retracting the clipping instrument out of the forceps channel. Such a clipping instrument is disclosed in Japanese Patent Provisional Publication No. 2006-87537, for example.

In the above referenced publication, a distal end of an inserted portion of the endoscope is provided with a bendable portion, which can be bended in an arbitrary angle through a remote operation, and the forceps channel to penetrate through the bendable portion is provided so that the clipping instrument can be inserted therethrough.

Figure 9:
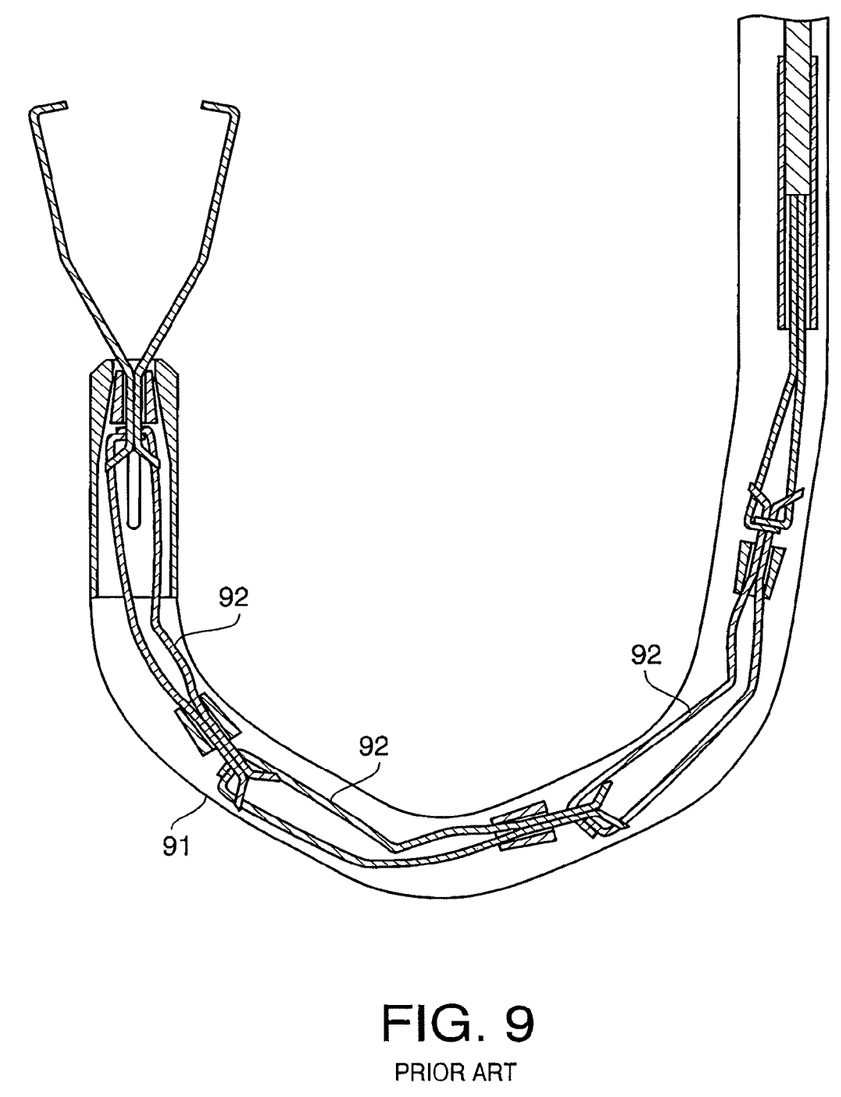
FIG. 9 is a schematic cross-sectional side view of a conventional clipping instrument being bended inside a flexible sheath of an endoscope.

In this configuration, when the bendable portion is bended at a large angle with a small curvature radius, the clipping instrument is bended at the same angle accordingly. FIG. 9 is a schematic cross-sectional side view of a conventional clipping instrument being bended inside the flexible sheath of an endoscope. As shown in FIG. 9, the clipping instrument can be strained, and each clip 92 aligned in line inside the flexible sheath 91 can be deformed to an excessive extent and damaged.

SUMMARY OF THE INVENTION

In view of the foregoing drawbacks, the present invention is advantageous in that an endoscopic surgical device with a clipping instrument, in which clips are durable for bending motions of a flexible sheath, is provided.

According to an aspect of the present invention, there is provided a clipping instrument for an endoscope. The clipping instrument includes a flexible sheath to be inserted into an instrument channel of the endoscope, at least one clip assembly, including a pair of openable and closable clipping arms, which is arranged in vicinity to a distal end portion of the flexible sheath with the clipping arms closed. The clipping arms are configured to be protruded forward to open outside the flexible sheath and to be closed to clip onto a treatment object outside the flexible sheath. The clipping instrument further includes an operating wire, which is configured to be forwarded and retracted to operate the pair of arms to be opened and closed. The at least one clip assembly is provided with a bendable portion, which corresponds to a position of a shaft to support the clipping arms, in an intermediate position between a distal end and a proximal end of the at least one clip assembly so that the at least one clip assembly can be arbitrarily bended at the bendable portion.

Optionally, the pair of clipping arms may be formed between the distal end of the at least one clip assembly and the bendable portion and rotatable about the shaft to open and close. The at least one clip assembly may further include a tail portion, which is formed between the bendable portion and the proximal end of the at least one clip assembly. The tail portion may provide connection between the operating wire and the pair of arms.

Optionally, a plurality of clip assemblies may be aligned to be mutually connected in vicinity to the distal end portion of the flexible sheath. The tail portion of one of the clip assemblies positioned closer to the distal end of the flexible sheath may be coupled with a distal part of another one of the clip assemblies positioned closer to the proximal end of the flexible sheath when the clip assemblies are mutually connected inside the flexible sheath.

According to another aspect of the present invention, there is provided a clip assembly for an endoscopic surgical instrument. The clip assembly includes a pair of clipping arms, which is openable and closable according to an operation to an operating wire being connected with the pair of clipping arms, arranged in vicinity to a distal end portion of a flexible sheath with the clipping arms closed, and configured to be protruded forward to open outside the flexible sheath and to be closed to clip onto a treatment object outside the flexible sheath. The clip assembly further includes a bendable portion, which corresponds to a position of a shaft to support the clipping arms, in an intermediate position between a distal end and a proximal end of the clip assembly so that the clip assembly can be arbitrarily bended at the bendable portion.

Optionally, the pair of clipping arms may be formed between the distal end of the clip assembly and the bendable portion and rotatable about the shaft to open and close. The clip assembly may further include a tail portion, which is formed between the bendable portion and the proximal end of the clip assembly. The tail portion may provide connection between the operating wire and the pair of arms.

DETAILED DESCRIPTION OF THE EMBODIMENT

Figure 1:
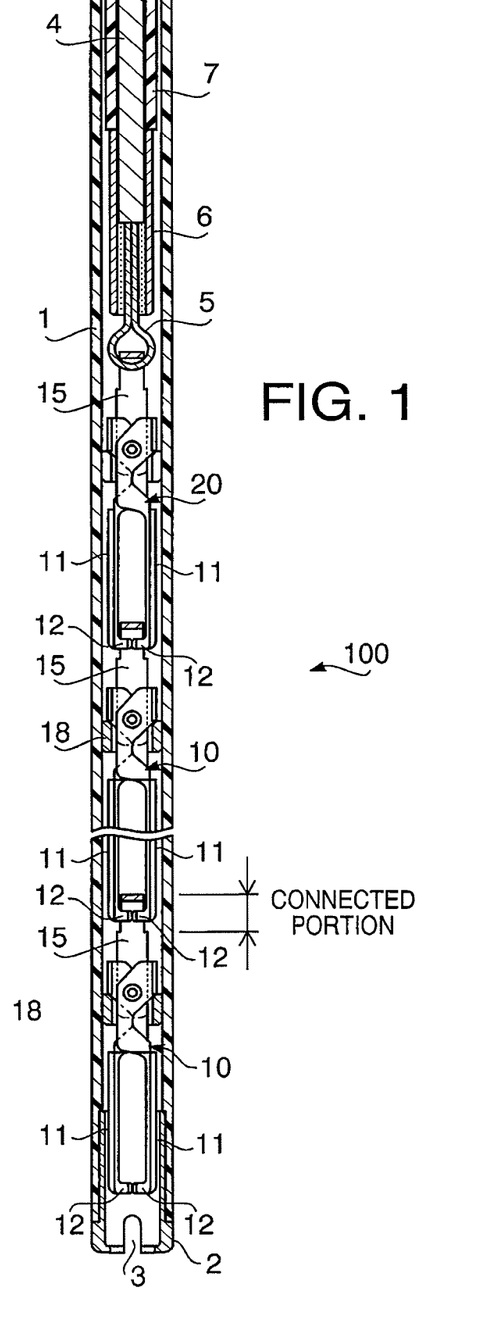
FIG. 1 is a cross-sectional side view of a clipping instrument for an endoscope according to an embodiment of the present invention.

Hereinafter, referring to the accompanying drawings, an illustrative embodiment of the invention will be described. FIG. 1 is a cross-sectional side view of a clipping instrument 100 for an endoscope (not shown) according to an embodiment of the present invention. The clipping instrument 100 includes a tubular flexible sheath 1. The flexible sheath 1 is made of, for example, poly-tetra-fluoro-ethylene and is inserted into a forceps channel (not shown) of the endoscope.

The flexible sheath 1 is provided with a resilient sleeve 2, which is formed to be substantially cylindrical, fixed to a distal end of the flexible sheath 1, and is made of a metal. An inner diameter of the sleeve 2 is substantially equivalent to an inner diameter of the flexible sheath 1 and is formed to be substantially smaller at a distal end portion of the sleeve 2.

The sleeve 2 is further formed to have a plurality (for example, three or four) of slits 3, which are parallel to an axial direction thereof at the distal end portion. With these slits 3, the sleeve 2 can be deformed radially outwardly at the distal end portion.

Inside the flexible sheath 1, an operating wire 4 to be advanced and retracted in parallel with an axial direction of the flexible sheath 1 is provided. The operating wire 4 is connected to an operating unit (not shown) at a proximal end thereof and can be advanced and retracted in accordance with an operation given to the operating unit. The operating wire 4 is fixedly connected to a connecting loop 5 through a connecting pipe 6. Further, a covering tube 7 is provided to surround the operating wire 4.

Figure 2:
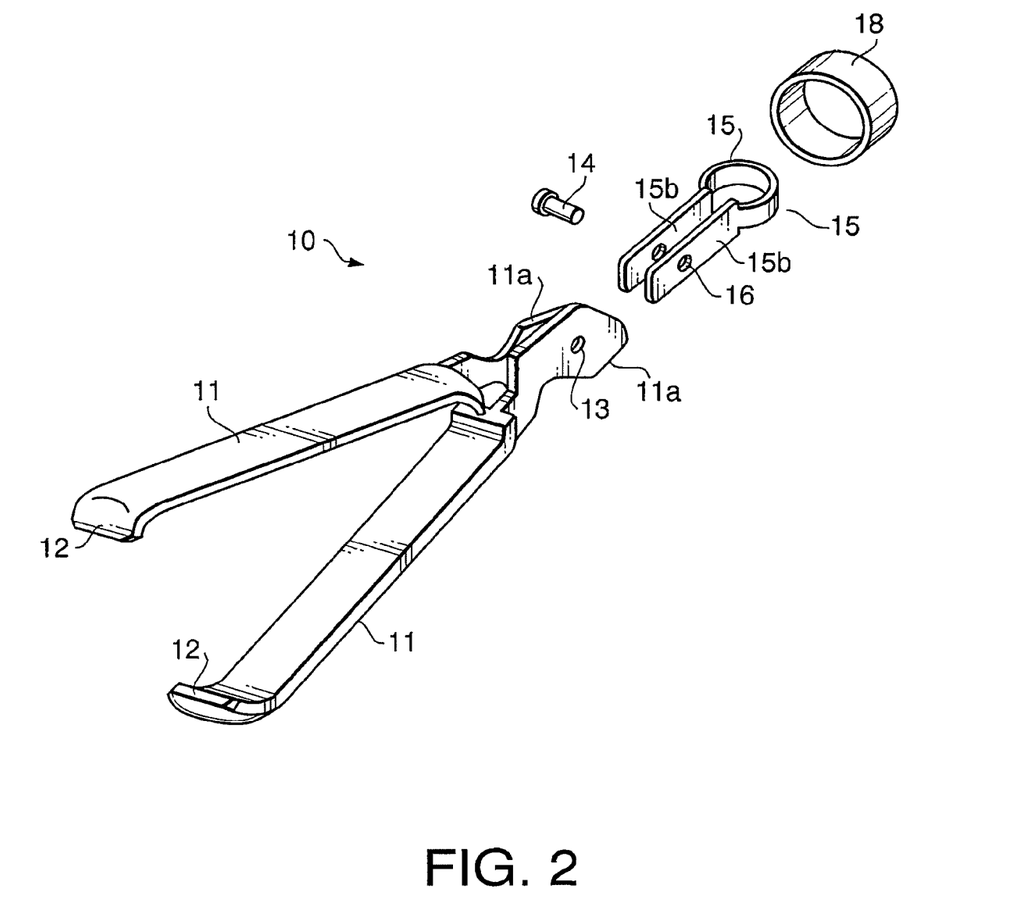
FIG. 2 is an exploded perspective view of a clip assembly of the clipping instrument according to the embodiment of the present invention.
Figure 3:
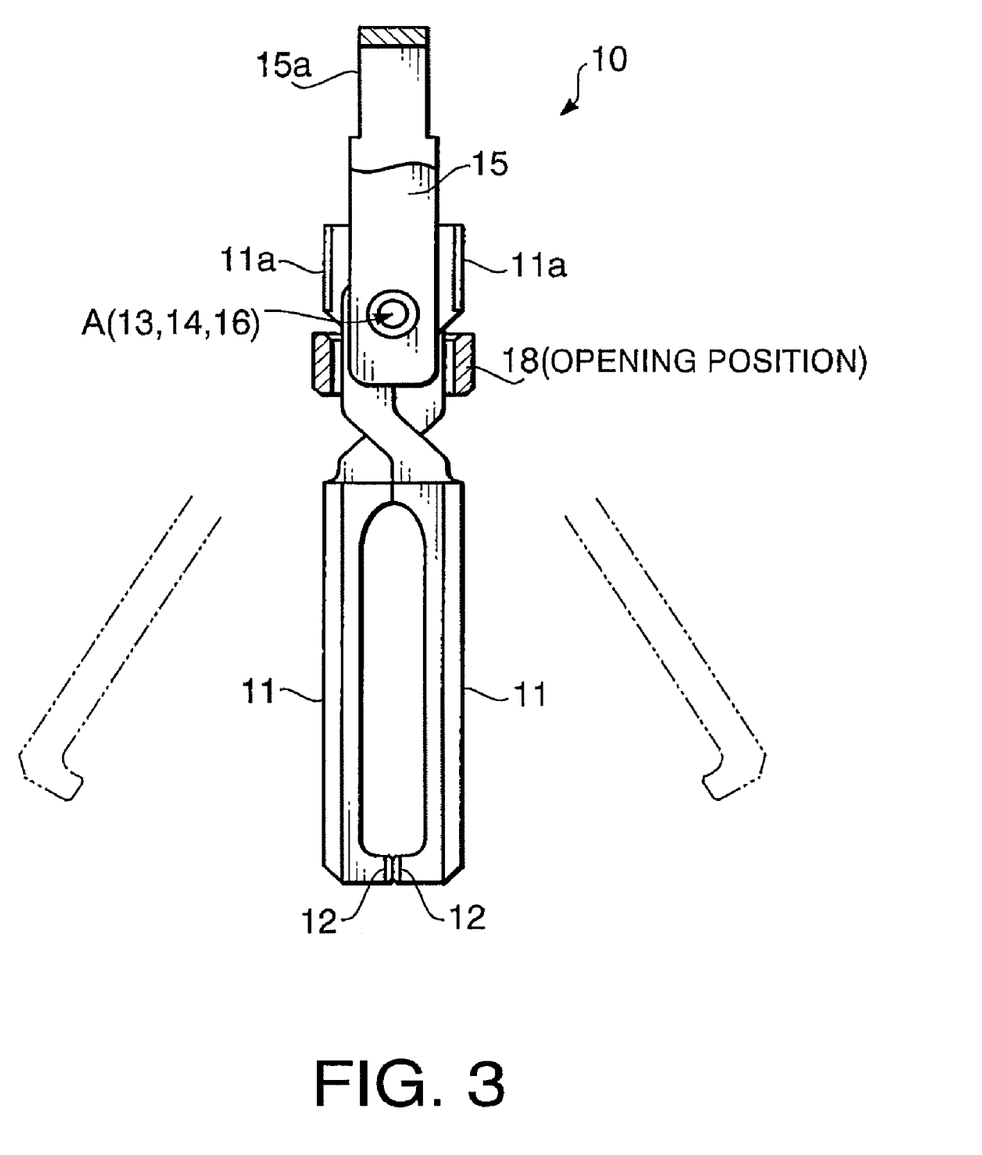
FIG. 3 is a side view of the clip assembly of the clipping instrument according to the embodiment of the present invention.

Further inside the flexible sheath 1, in vicinity to a distal end portion thereof, a plurality (for example, from two to four) clip assemblies 10 are aligned in line. FIG. 2 is an exploded perspective view of the clip assembly 10 of the clipping instrument 100 according to the embodiment of the present invention. FIG. 3 is a side view of the clip assembly 10 of the clipping instrument 100 according to the embodiment of the present invention. The clip assembly 10 is provided with a pair of arms 11, each of which is individually formed and provided with a claw portion 12. The claw portion 12 is curved inward, when the arms 11 are assembled, so that the two claw portions 12 are opposed to each other to clutch a treatment object.

Each of the arms 11 is formed to have a through hole 13 in vicinity to a proximal end thereof. A shaft 14 supporting the arms 11 is penetrated through the through holes 13 of the arms 11 so that the arms 11, rotated about the shaft 14, can be arbitrarily opened (as indicated in dashed two-dotted lines in FIG. 3) and closed (as indicated in solid lines in FIG. 3.)

The clip assembly 10 is further provided with a tail portion 15, which includes an open-ringed connecting loop 15a at a proximal end thereof, a pair of plate portions 15b, which are parallel to each other and loosely sandwich the proximal end portion of the arms 11 therebetween, and through holes 16 through which the shaft 14 is penetrated. The tail portion 15 is connected to the operating wire 4 through another clip assembly 10 being aligned at a proximal side and a connecting clip 20, which will be described later.

Furthermore, the clip assembly 10 includes a fastening ring 18, by which the arms 11 are forcibly closed. When the arms 11 are allowed to open, the fastening ring 18 is loosely fit around the proximal portion of the arms 11, as shown in FIG. 3.

Figure 4:
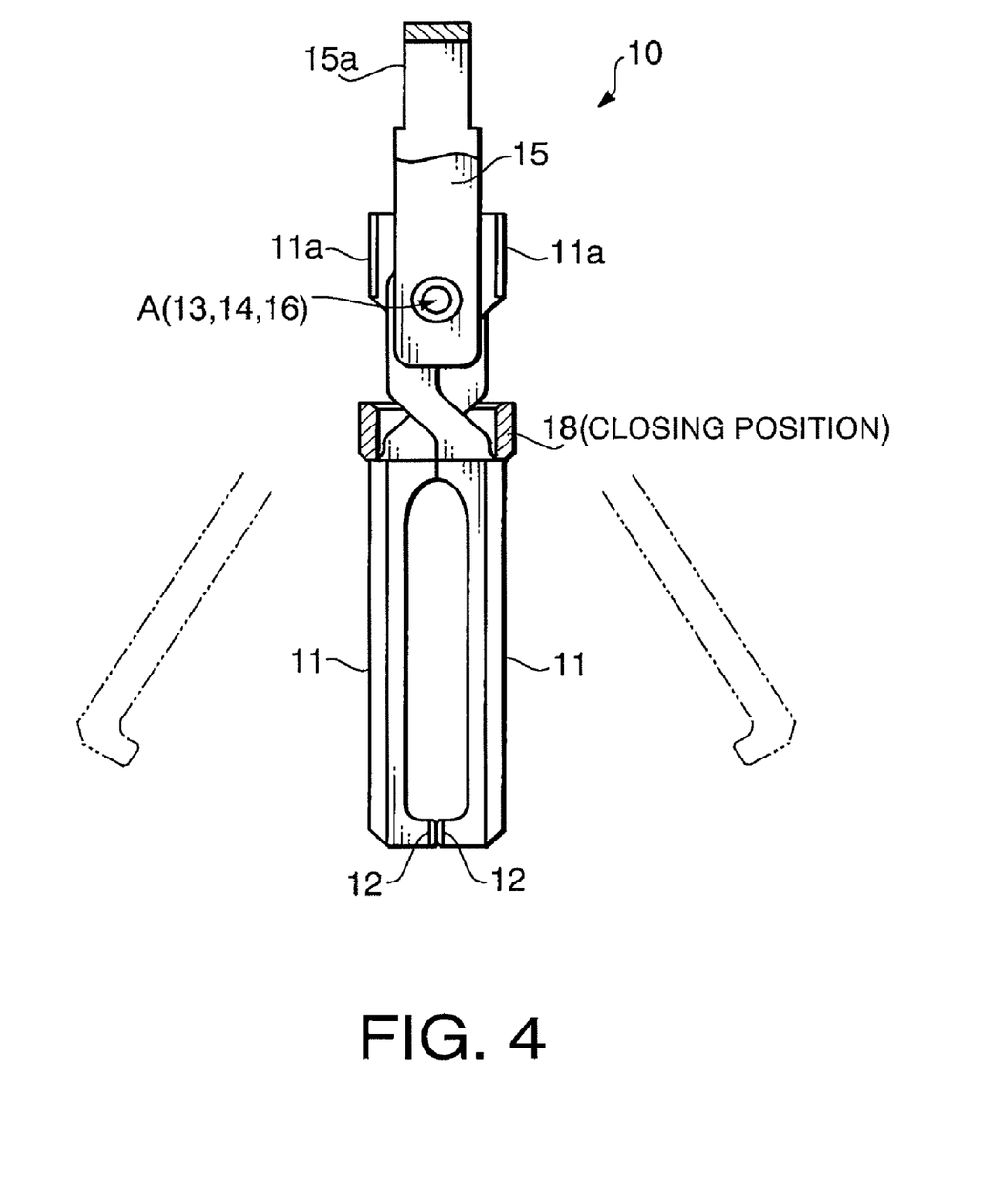
FIG. 4 is a side view of the clip assembly of the clipping instrument being closed according to the embodiment of the present invention.

FIG. 4 is a side view of the clip assembly 10 of the clipping instrument 100 being closed according to the embodiment of the present invention. As the fastening ring 18 is forwarded from an opening position shown in FIG. 3 to a closing position shown in FIG. 4, the arms 11 are forcibly closed. When the fastening ring 18 is retracted rearward to the opening position, in which the fastening ring 18 becomes in contact with plate portions 11a of the arms 11. Thus, the arms 11 are opened.

In addition to the above configuration, the clip assembly 10 is formed to have a rotating portion A in an intermediate position between the distal end and the proximal end of the clip assembly 10. Therefore, the components of the clip assembly 10 located in positions closer to the distal end of the clip assembly 10 with respect to the shaft 14 can be rotated about the shaft 14 regardless of the open/close motions of the arms 11, i.e., the clip assembly 10 can be bended at the rotating portion A. Meanwhile, the components located in positions closer to the proximal end of the clip assembly 10 with respect to the shaft 14 form the tail portion 15, by which the clip assembly 10 is connected with the operating wire 4.

Figure 5:
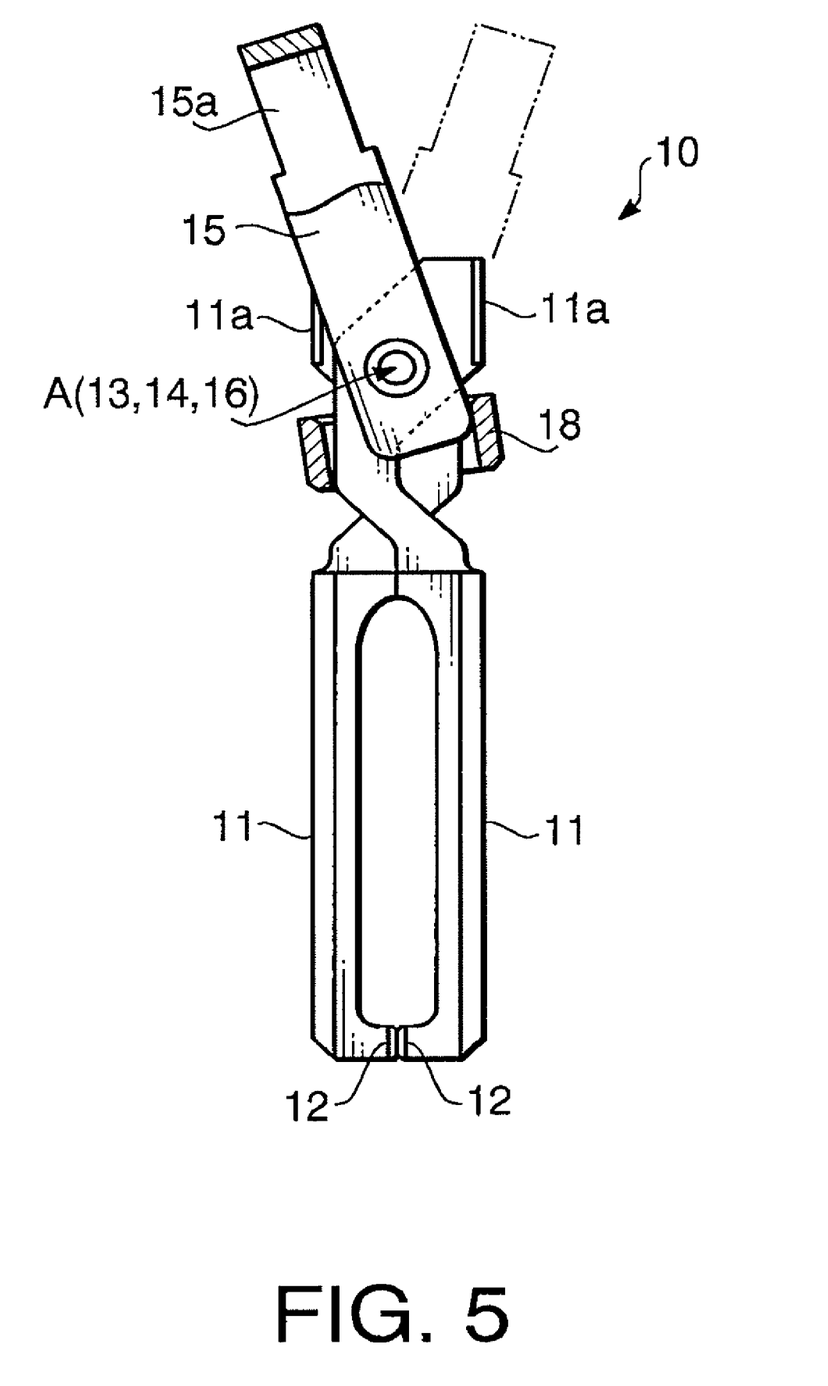
FIG. 5 is a side view of the clip assembly of the clipping instrument with arms being rotated about the rotating portion according to the embodiment of the present invention.

FIG. 5 is a side view of the clip assembly 10 of the clipping instrument 100 with the arms 11 being rotated about the rotating portion A according to the embodiment of the present invention. The arms 11 can be rotated arbitrarily about the rotating portion A with respect to the tail portion 15.

Referring back to FIG. 1, in the flexible sheath 1 at the distal end portion, the clip assemblies 10 aligned in line are mutually connected. More specifically, the tail portion 15 of the clip assembly 10 in a position closer to the distal end of the flexible sheath 1 (front side) and the arms 11 of the clip assembly 10 in a position closer to the proximal end of the flexible sheath 1 (rear side) define a connected portion. The claw portions 12 of the arms 11 of the clip assembly 10 in the rear side are closed to clutch the connecting loop 15a of the clip assembly 10 positioned in the front side.

The clipping instrument 100 includes an undetachable clip assembly 20, which is undetachably connected to the connecting loop 5. Unlike the clip assemblies 10, the undetachable clip assembly 20 does not include the fastening ring 18, however, the remaining configuration of the detachable clip assembly 20 is identical to the clip assembly 10. The undetachable clip assembly 20 is connected to the tail portion 15 of the clip assembly 10 being located at the rear end of the aligned clip assemblies 10, i.e., the arms 11 of the undetachable clip assembly 20 are closed to clutch the tail portion 15 of the clip assembly 10 at the rear end.

The arms 11 of the plurality of mutually connected clip assemblies 10 and the undetachable clip assembly 20 are closed inside the flexible sheath 1 so that the clipping instrument 100 is inserted into the forceps channel of the endoscope. As the clipping instrument 100 is advanced through a curved portion inside a body, the flexible sheath 1 including the clipping instrument 10 is curved accordingly.

Figure 6:
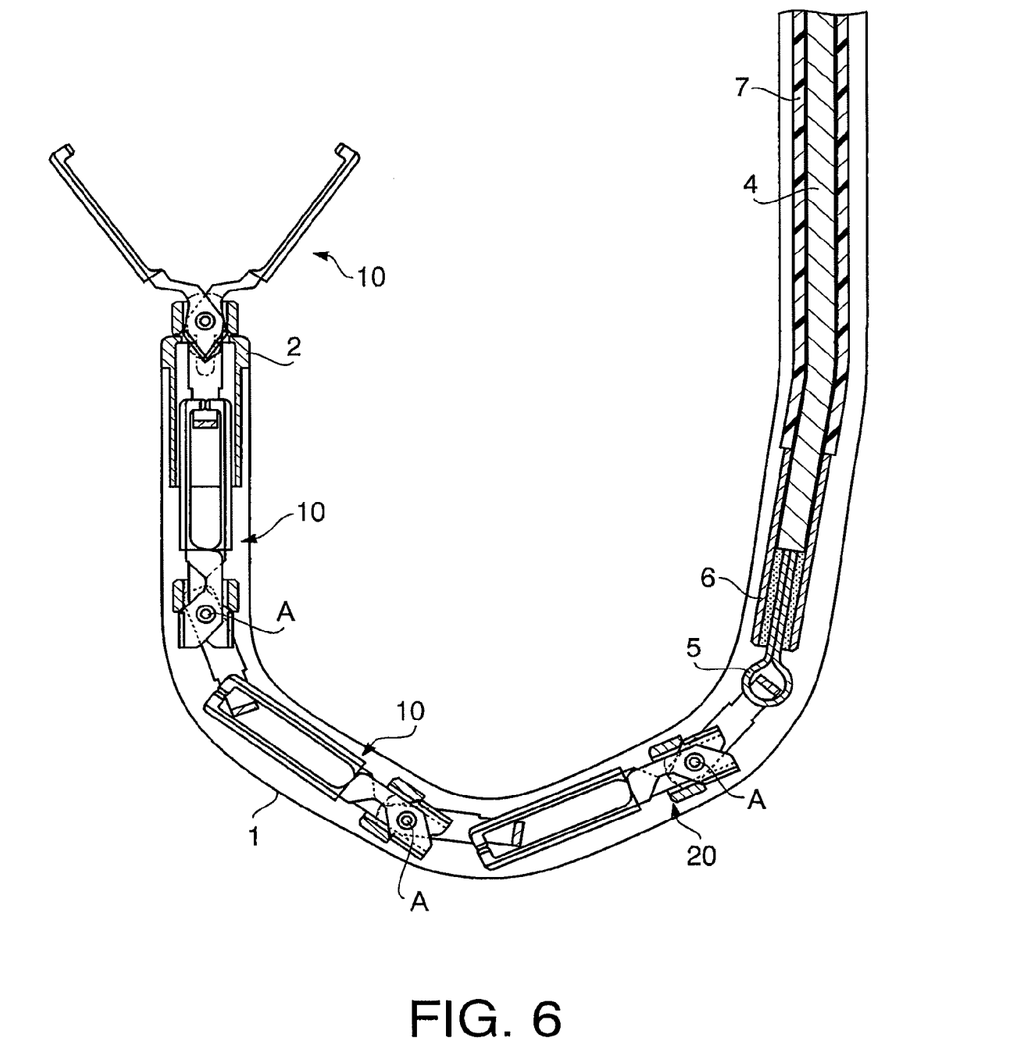
FIG. 6 is a schematic cross-sectional side view of the clipping instrument being curved inside a flexible sheath of the endoscope according to the embodiment of the present invention.

FIG. 6 is a schematic cross-sectional side view of the clipping instrument 100 being curved at a large angle with a small curvature radius inside the flexible sheath 1 of the endoscope according to the embodiment of the present invention. With the above configuration of the clipping instrument 100, however, each of the clip assemblies 10 is bended at the rotating portion A. In addition, the connected clip assemblies 10 and the undetachable clip assembly 20 can be bended at the connected portions, in which the claw portions 12 of the arms 11 of the clip assembly 10 (undetachable clip assembly 20) in the rear side clutch the tail portion 15 of the clip assembly 10 (undetachable clip assembly 20) in the front side. Therefore, the aligned clip assemblies 10 can be bended at the large angle with the small curvature radius without being damaged so that the clipping operations can be conducted in a less troublesome manner.

Figure 7:
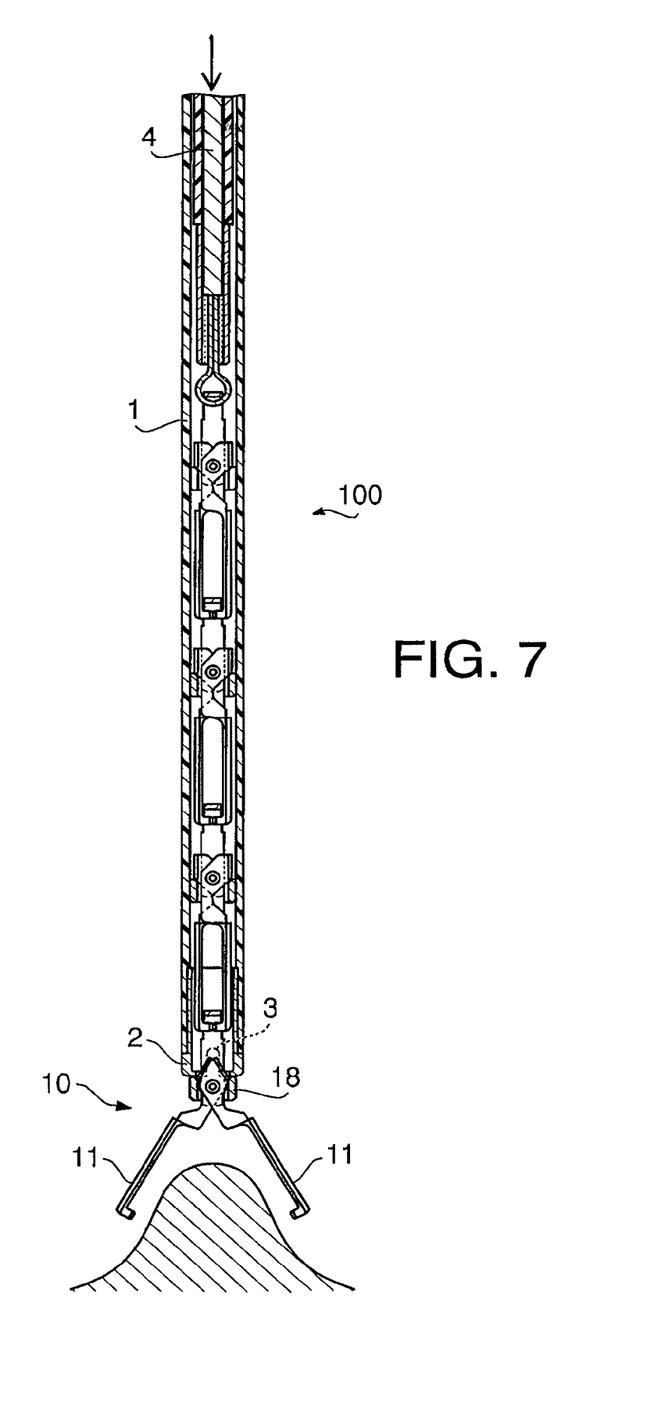
FIG. 7 is a schematic cross-sectional side view of the clipping instrument being in a first half of a clipping motion according to the embodiment of the present invention.

FIG. 7 is a schematic cross-sectional side view of the clipping instrument 100 being in a first half of a clipping motion of the clipping operation according to the embodiment of the present invention. In the clipping operation, firstly, the operating wire 4 is forwarded to the distal end of the flexible sheath 1. Accordingly, the arms 11 and the fastening ring of the clip assembly 10 at the front end are protruded through the sleeve 2. As the fastening ring 18 penetrates through, the slits 3 of the sleeve 2 are expanded so that the sleeve 2 is resiliently deformed. As the fastening ring 18 is further forwarded to eject entirely from the sleeve 2, the sleeve 2 recovers to its original shape, which does not allow the fastening ring 18 to be pulled back inside the flexible sheath 1. Thus, the arms 11 are opened outside the sleeve 2 and the flexible sheath 1.

Figure 8:
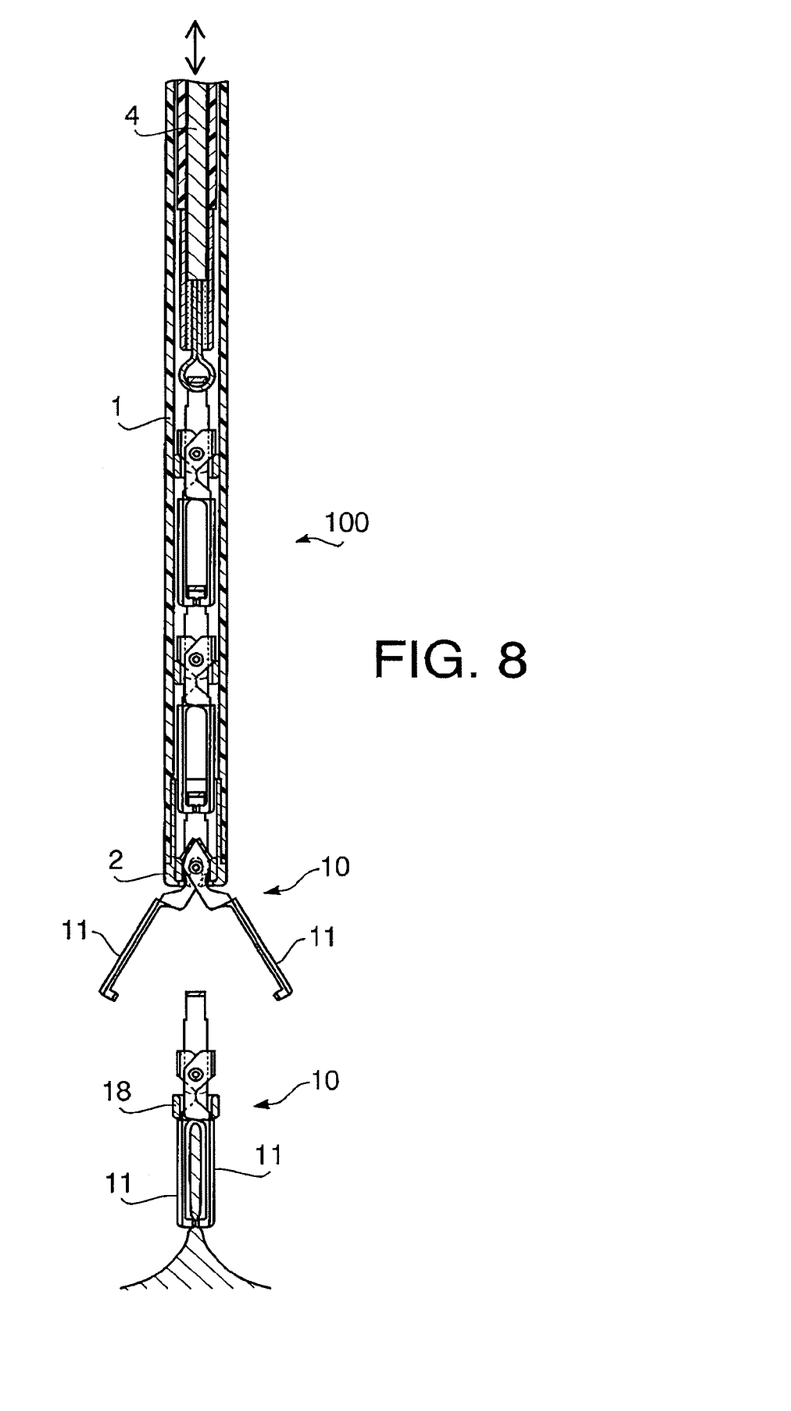
FIG. 8 is a schematic cross-sectional side view of the clipping instrument being in a second half of the clipping motion according to the embodiment of the present invention.

With the arms 11 opened as above, secondly, when the operating wire 4 is withdrawn rearward, the arms 11 are retracted in the fastening ring 18 and closed accordingly. Thus, a desired portion of in vivo tissue can be clutched between the claw portions 12. FIG. 8 is a schematic cross-sectional side view of the clipping instrument 100 being in a second half of the clipping motion according to the embodiment of the present invention. With the arms 11 of the clip assembly 10 at the front end being closed, when the operating wire 4 is forwarded once more, the clip assembly 10 at the second from the front end is penetrated through the sleeve 2, and the arms 11 of the second clip assembly 10 are opened. Accordingly, the first clip assembly 10 at the front end is released from the second clip assembly 10 with the arms 11 being closed. the clipping operation for the second and the following clip assemblies 10 are conducted similarly.

With the above configuration, an endoscopic surgical device with a clipping instrument, in which clip assemblies are durable for bending motions of a flexible sheath, can be provided.

Although an example of carrying out the invention has been described above, the present invention is not limited to the above described embodiment. For example, a single clip assembly 10 may be provided instead of two or more clip assemblies 10 in the clipping instrument 100.

The present disclosure relates to the subject matter contained in Japanese Patent Application No. P2006-303459, filed on Nov. 9, 2006, which is expressly incorporated herein by reference in its entirety.

What is claimed is:

1. A clipping instrument for an endoscope, comprising:
a flexible sheath to be inserted into an instrument channel of the endoscope;
at least one clip assembly including a pair of clipping arms rotatable about a shaft that supports the pair of clipping arms to open and close, the pair of clipping arms having at least a first through hole, the at least one clip assembly being arranged in vicinity to a distal end portion of the flexible sheath with the clipping arms closed, wherein the pair of clipping arms are configured to be protruded forward to open outside the flexible sheath and to be closed to clip onto a treatment object outside the flexible sheath;
an operating wire configured to be forwarded and retracted to operate the pair of clipping arms to be opened and closed; and
the at least one clip assembly being provided with a bendable portion, the bendable portion provided at a position of the shaft and intermediate a distal end and a proximal end of the at least one clip assembly so that the at least one clip assembly can be arbitrarily bended at the shaft,
the pair of clipping arms formed between the distal end of the at least one clip assembly and the bendable portion,
the at least one clip assembly including a tail portion formed between the bendable portion and the proximal end of the at least one clip assembly, the tail portion including a plate portion having at least a second through hole, and the tail portion connecting the operating wire and the pair of arms, wherein the shaft extends through the first and second through holes thereby supporting the pair of clipping arms to open and close; and the at least one clip assembly comprising a plurality of clip assemblies aligned to be mutually connected in vicinity to the distal end portion of the flexible sheath, and wherein the tail portion of one of the clip assemblies positioned closer to a most distal end of the flexible sheath is coupled with a distal part of another one of the clip assemblies positioned closer to a most proximal end of the flexible sheath when the clip assemblies are mutually connected inside the flexible sheath.

2. A clip assembly for an endoscopic surgical instrument, comprising:
a pair of clipping arms rotatable about a shaft that supports the pair of clipping arms to open and close according to an operation of an operating wire connected with the pair of clipping arms, the pair of clipping arms having at least a first through hole, the pair of clipping arms being arranged in vicinity to a distal end portion of a flexible sheath with the pair of clipping arms closed, and wherein the pair of clipping arms are configured to be protruded forward to open outside the flexible sheath and to be closed to clip onto a treatment object outside the flexible sheath;
a bendable portion provided at a position of the shaft and intermediate a distal end and a proximal end of the clip assembly so that the clip assembly can be arbitrarily bended at the shaft,
the pair of clipping arms formed between the distal end of the clip assembly and the bendable portion,
the clip assembly including a tail portion formed between the bendable portion and the proximal end of the clip assembly, the tail portion including a plate portion having at least a second through hole, and
the tail portion connecting the operating wire and the pair of arms, wherein the shaft extends through the first and second through holes thereby supporting the pair of clipping arms to open and close; and the clip assembly comprising a plurality of clip assemblies aligned to be mutually connected in vicinity to the distal end portion of the flexible sheath, and wherein the tail portion of one of the clip assemblies positioned closer to a most distal end of the flexible sheath is coupled with a distal part of another one of the clip assemblies positioned closer to a most proximal end of the flexible sheath when the clip assemblies are mutually connected inside the flexible sheath.

* * * * *